(12) United States Patent
Weimer

(10) Patent No.: US 6,531,278 B1
(45) Date of Patent: Mar. 11, 2003

(54) LIGAND-DNA COMPOSITION FOR CAPTURE AND DETECTION OF CONTAMINANTS ON A SOLID SURFACE

(75) Inventor: Bart Weimer, Logan, UT (US)

(73) Assignee: Utah State University, North Logan, UT (US)

( * ) Notice: Subject to any disclaimer, the term of this patent is extended or adjusted under 35 U.S.C. 154(b) by 0 days.

(21) Appl. No.: 09/231,604

(22) Filed: Jan. 14, 1999

Related U.S. Application Data

(60) Provisional application No. 60/071,339, filed on Jan. 14, 1998.

(51) Int. Cl.⁷ .......................... C07K 16/00; C12Q 1/68; G01N 33/53; G01N 33/543
(52) U.S. Cl. .................... 435/6; 435/7.1; 435/7.92; 435/7.94; 435/962; 435/971; 435/972; 436/518; 436/524; 436/525; 436/527; 436/528; 436/529; 436/531; 436/532; 436/536; 436/538; 436/164; 436/172; 436/824; 530/391.1; 530/391.3; 530/391.5; 530/413
(58) Field of Search .................... 435/6, 7.1, 7.92, 435/7.94, 962, 971, 972; 436/518, 524, 525, 527, 528, 529, 531, 532, 536, 538, 164, 172, 824; 530/391.1, 391.3, 391.5, 413; 935/77, 78

(56) References Cited

U.S. PATENT DOCUMENTS 4,152,411 A * 5/1979 Schall
4,996,142 A * 2/1991 Al-Hakim et al. ............. 435/6
5,556,752 A * 9/1996 Lockhart et al. ............... 435/6
5,565,324 A * 10/1996 Still et al. ....................... 435/6
5,789,165 A * 8/1998 Oku et al. ....................... 435/6

FOREIGN PATENT DOCUMENTS

WO 91/08307 * 6/1991
WO 94/27150 * 11/1994

* cited by examiner

*Primary Examiner*—Christopher L. Chin
*Assistant Examiner*—James L. Grun
(74) *Attorney, Agent, or Firm*—Clayton, Howarth & Cannon, P.C.

(57) ABSTRACT

Compositions and methods of use thereof for capture and detection of selected molecules are described. In one embodiment, a first composition includes a ligand component, such as an antibody coupled to a nucleic acid component. An a preferred embodiment, the nucleic acid is labeled with a fluorescent marker to facilitate detection. Another aspect of the invention is the ligand component bound to a solid support via a complementary nucleic acid component and a linker moiety. The method involves binding the target with the first composition in free solution, then binding the target to the solid support by means of both DNA hybridization and antibody-antigen affinity binding. Unbound molecules are washed away, and then the bound targets are detected by fluorescence detection. Vital stains can also be used to detect viable cells.

20 Claims, 2 Drawing Sheets

LIGAND-DNA COMPOSITION FOR CAPTURE AND DETECTION OF CONTAMINANTS ON A SOLID SURFACE

CROSS-REFERENCE TO RELATED APPLICATIONS

This application claims the benefit of U.S. Provisional Application Ser. No. 60/071,339, filed Jan. 14, 1998.

BACKGROUND OF THE INVENTION

This invention relates to capture of a target entity on a solid phase and detection of the captured target. More particularly, the invention relates to capture and detection of contaminants in biomedical, environmental, and food samples.

Considerable progress in the development of detectors of microbial contamination has been achieved in recent years. These detectors can be applied to medical, process control, and environmental fields. Such detectors must possess features such as high specificity, simplicity, sensitivity, speed, reliability, and reproducibility. S. Y. Rabbany et al., Optical Immunosensors, 22 Crit. Rev. Biomed. Engin. 307–346 (1994). With the use of antibodies as the ligands for specific capture, numerous applications have been developed for detection of pathogenic bacteria. M. R. Blake & B. C. Weimer, Immunomagnetic Detection of *Bacillus stearothermophilus* Spores in Food and Environmental Samples, 63 J. Appl. Environ. Microbiol. 1643–1646 (1997); A. Burkowski, Rapid Detection of Bacterial Surface Proteins Using an Enzyme-linked Immunosorbent Assay System, 34 J. Biochem. Biophys. Methods 69–71 (1997); S. Chen et al., A Rapid, Sensitive and Automated Method for Detection of Salmonella Species in Foods Using AG-9600 AmpliSensor Analyzer, 83 J. Appl. Microbiol. 314–321 (1997); L. S. Metherell et al., Rapid, Sensitive, Microbial Detection by Gene Amplification Using Restriction Endonuclease Target Sequence, 11 Mol. Cell Probes 297–308 (1997); F. Roth et al., A New Multiantigen Immunoassay for the Quantification of IgG Antibodies to Capsular Polysaccharides of *Streptococcus pneumoniae*, 176 J. Inf. Dis. 526–529 (1997).

Bacterial spores are the most heat-stable form of microorganisms, are ubiquitous in the environment, and therefore are of great concern in food products, such as milk, that receive extensive heat treatments to prolong shelf life. Spore counts in milk from around the world vary between zero and >22,000 colony forming units (cfu)/ml depending on the climate of the region. S. Chen, supra. *Bacillus stearothermophilus* spores are among the most heat-resistant spores and are found in high numbers in soil and water. *B. stearothermophilus* spores survive extreme heat and will germinate and grow at elevated product storage temperatures, which occur in foods transported in equatorial regions of the world.

While *B. stearothermophilus* is not commonly a problem, other bacilli often lead to food-borne illness or spoilage in a variety of foods. *Bacillus cereus*, *B. licheniformis*, *B. subtilis*, and *B. pumilus*, have all been implicated in outbreaks of food-borne illness and are commonly isolated from raw and heat-treated milk. M. W. Griffiths, Foodborne Illness Caused by Bacillus spp. Other than *B. cereus* and Their Importance to the Dairy Industry, 302 Int. Dairy Fed. Bulletin 3–6 (1995). *B. cereus* is also responsible for a sweet curdling defect in milk, as well as being pathogenic. W. W. Overcast & K. Atmaram, The Role of *B. cereus*, in Sweet Curdling of Fluid Milk, 37 J. Milk Food Technol. 233–236 (1973). A mesophilic heat-resistant bacillus similar to Bacillus badius, has been isolated from extreme-temperature-processed milk ($D_{147}$=5 sec). P. Hammer et al., Pathogenicity Testing of Unknown Mesophilic Heat Resistant Bacilli from UHT-milk, 302 Int. Dairy Fed. Bulletin 56–57 (1995). *B. badius* is a mesophilic organism that grows readily at room temperature, making it a likely candidate for spoiling temperature-processed foods. There have been 52 confirmed cases of *B badius* in ultra-high-temperature treated milk in Europe and two cases outside Europe. Lack of a rapid spore assay that can be used in milk contributes to the difficulty of prediction of post-processing spoilage, thereby limiting the shelf life and product safety. H. Hofstra et al., Microbes in Food-processing Technology, 15 FEMS Microbiol. Reviews 175–183 (1994). Such an assay could be used in a hazard critical control point (HACCP) plan allowing raw materials with high spore loads to be diverted to products that do not pose a food safety risk to consumers.

The standard method for quantifying spores in milk, G. H. Richardson, Standard Methods for the Examination of Dairy Products (15$^{th}$ ed., 1985), involves heat-shock and an overnight plate count. This method is time-consuming and merely yields historical information. The food industry needs microbiological assays to yield predictive information for maximum benefit in HACCP analysis and risk assessment. An enzyme-linked immunosorbent assay (ELISA) capable of detecting >$10^6$ cfu/ml of *B. cereus* spores in food has been reported, but was unacceptable due to antibody cross reactivity. L. A. Metherell et al., supra.

Techniques to increase sensitivity of immunosorbent assays have focused on more efficient reporter labels, such as faster catalyzing reporter-enzymes; signal amplification, such as avidin- or streptavidin-biotin enzyme complexes; and better detectors, such as luminescence and fluorescence. L. J. Kricka, Selected Strategies for Improving Sensitivity and Reliability of Immunoassays, 40 Clin. Chem. 347–357 (1994); W. W. Overcast & K. Atmaram, supra. Immunomagnetic antigen capture is used extensively to separate and identify *Escherichia coli* and Salmonella from foods. M. R. Blake & B. C. Weimer, supra; S. Y. Rabbany et al., supra; C. Blackburn et al., Separation and Detection of Salmonellae Using Immunomagnetic Particles, 5 Biofouling 143–156 (1991); P. M. Fratamico et al., Rapid Isolation of *Escherichia coli* O157:H7 from Enrichment Cultures of Foods Using an Immunomagnetic Separation Method, 9 Food Microbiol. 105–113 (1992); A Lund et al., Rapid Isolation of K88$^+$*Escherichia coli* by using Immunomagnetic Particles, 26 J. Clin. Microbiol. 2572–2575 (1988); L. P. Mansfeild & S. J. Forsythe, Immunomagnetic Separation as an Alternative to Enrichment Broths for Salmonella Detection, 16 Letters Appl. Microbiol. 122–125 (1993); A. J. G. Okrend et al., Isolation of *Escherichia coli* O157:H7 using O157 Specific Antibody Coated Magnetic Beads, 55 J. Food Prot. 214–217 (1992); Skjerve & Olsvic, Immunomagnetic Separation of Salmonella from Foods, 14 Inter. J. Food Microbiol. 11–18 (1991); D. J. Wright et al., Immunomagnetic Separation as a Sensitive Method for Isolating *Escherichia coli* O157 from Food Samples, 113 Epidemiol. Infect. 31–39 (1994). These methods, however, involve either a pre-incubation or a subsequent incubation step (usually *18–24* hours) to increase the cell numbers for detection. Immunomagnetic capture greatly shortens *E. coli* and Salmonella testing, but long incubation times limit this method for predictive information. Immunocapture has also been used to quantitate *Bacillus anthracis* spores in soil samples using luminescence detection, A. Burkowski, supra, but these efforts have led to tests that have a detection limit of about $10^3$ cfu/ml.

In view of the foregoing, it will be appreciated that providing compositions and methods for capture and detection of selected contaminants would be a significant advancement in the art.

BRIEF SUMMARY OF THE INVENTION

It is an object of the present invention to provide compositions and methods of use thereof for capture and detection of contaminants in food, environmental samples, and other applications.

It is another object of the invention to provide compositions and methods of use thereof for capture and detection of contaminants, wherein such methods are highly specific, simple, sensitive, rapid, reliable, and reproducible.

These and other objects can be achieved by providing a composition of matter comprising a ligand component covalently bonded to a nucleic acid component. Preferably, the ligand component is a member selected from the group consisting of antibodies, antigens, lectins, saccharides, and gangliosides, and more preferably is an antibody. In a preferred embodiment, the nucleic acid component is an oligonucleotide. In another preferred embodiment, a linker is interposed between the ligand component and the nucleic acid component. Preferably, the linker is a member selected from the group consisting of polythreonine, polyserine, and dextran, and more preferably is polythreonine. In yet another preferred embodiment, the invention further comprising a label member coupled to the nucleic acid component.

Another composition of matter comprises a solid support covalently bonded to a linker molecule, a nucleic acid component covalently bonded to the linker molecule, and a ligand component covalently bonded to the nucleic acid component. In one illustrative embodiment, the solid support is in the form of a membrane. Preferably, the membrane is a polymer, and more preferably is a member selected from the group consisting of fluorinated polymers, polyolefins, polystyrene, substituted polystyrenes, polysulfones, polyesters, polyacrylates, polycarbonates; vinyl polymers, copolymers of butadiene and styrene, fluorinated ethylene-propylene copolymers, ethylenechlorotrifluoroethylene copolymers, and mixtures thereof. In another preferred embodiment, the ligand component is a member selected from the group consisting of antibodies, antigens, lectins, saccharides, and gangliosides, and preferably is an antibody. Preferably, the nucleic acid component is an oligonucleotide, and the linker is a member selected from the group consisting of polythreonine, polyserine, and dextran, more preferably polythreonine. In another illustrative embodiment, the solid support is in the form of a bead. Preferably, such a bead is a member selected from the group consisting of silicon, glass, silica, quartz, metal oxides, polyvinyl alcohol, polystyrene, poly(acrylic acid), and mixtures thereof.

A method for capturing a target on a solid support comprises:

(a) mixing an aqueous sample containing the target with a first composition comprising a ligand component, configured for binding the target, covalently bonded to a first nucleic acid component such that the ligand component binds the target to result in a complex;

(b) contacting the complex with a second composition comprising (i) a solid support covalently bonded to a linker, (ii) a second nucleic acid component covalently bonded to the linker wherein the second nucleic acid component is complementary to at least a portion of the first nucleic acid component and hybridizes thereto when in contact therewith such that the resulting duplex has a thermal melting temperature of about 60–85° C., and (iii) the ligand component covalently bonded to the second nucleic acid component, such that the second nucleic acid component hybridizes to the first nucleic acid component and the ligand component of the second composition binds the target;

(c) heating the aqueous sample to a temperature above the thermal melting temperature of the duplex without denaturing the ligand component and causing the heated aqueous sample to flow by the solid support; and (d) then reducing the temperature of the aqueous sample to ambient temperature.

A method for detecting a target on a solid support comprises:

(a) mixing an aqueous sample containing the target with a first composition comprising (i) a ligand component, configured for binding the target, covalently bonded to (ii) a first nucleic acid component, and (iii) a label component, such that the ligand component binds the target to result in a complex;

(b) contacting the complex with a second composition comprising (i) a solid support covalently bonded to a linker, (ii) a second nucleic acid component covalently bonded to the linker wherein the second nucleic acid component is complementary to at least a portion of the first nucleic acid component and hybridizes thereto when in contact therewith such that the resulting duplex has a thermal melting temperature of about 60–85° C., and (iii) the ligand component covalently bonded to the second nucleic acid component, such that the second nucleic acid component hybridizes to the first nucleic acid component and the ligand component of the second composition binds the target;

(c) heating the aqueous sample to a temperature above the thermal melting temperature of the duplex without denaturing the ligand component and causing the heated aqueous sample to flow by the solid support; and (d) then reducing the temperature of the aqueous sample to ambient temperature; and (e) detecting the label component on the solid support.

DETAILED DESCRIPTION

Before the present compositions and methods of use thereof for capture and detection of selected entities are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out herein.

One problem that plagues solid phase capture is that the ligand or capturing molecule usually does not bind its target as efficiently when the ligand is bound to a solid phase as it does when the ligand is free in solution. This decreased activity leads to an inability to capture the target at low concentrations. The present invention overcomes this inadequacy by allowing the ligand to interact with the target in free solution.

Figure 1:
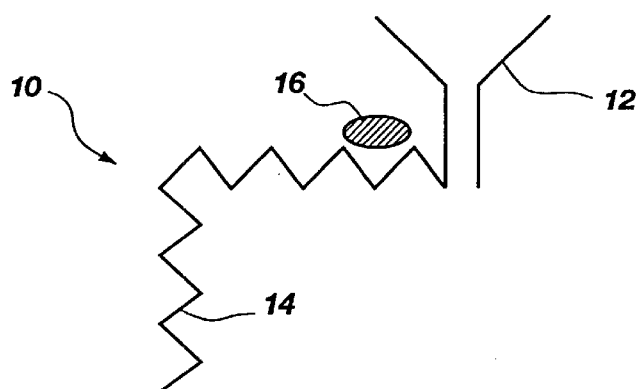
FIG. 1 shows a schematic diagram of an illustrative ligand-nucleic acid composition according to the present invention.

FIG. 1 shows a schematic representation of an illustrative composition according to the present invention for use in binding a ligand to a target in free solution. The composition 10 comprises a ligand member 12 covalently bonded to a nucleic acid member 14. In a preferred embodiment, the composition further comprises a label member 16, such as a fluorescent marker. Preferred ligands that can be used according to the present invention include antibodies, antigens, gangliosides, lectins, saccharides, and the like. For example, if the target is a protein or other molecule capable of eliciting an antibody response when injected into an appropriate warm-blooded animal, then the ligand can be an antibody configured for binding such target molecule. If the target is an antibody, then the ligand can be the cognate antigen for binding such antibody target. If the target is a saccharide, then an appropriate lectin can be used as a ligand, and vice versa. Other combinations of ligands and targets will be apparent to persons skilled in the art and are considered within the scope of the invention. Antibodies are especially preferred ligands. The nucleic acid member is preferably an oligonucleotide.

Figure 2:
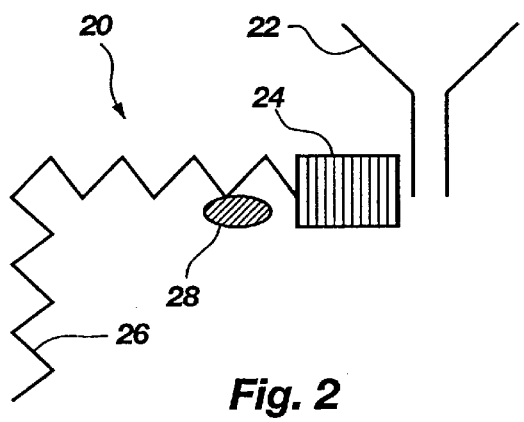
FIG. 2 shows a schematic diagram of another illustrative ligand-nucleic acid composition according to the present invention.

FIG. 2 illustrates an alternative configuration of a composition for binding a target in free solution. The composition 20 comprises a ligand 22 covalently bonded to a linker 24, which is in turn covalently bonded to a nucleic acid member 26. In a preferred embodiment, the composition can further comprise a label member 28. The ligand can be any of the ligands described above. Preferred linkers that can be used in the present invention include polythreonine, polyserine, and dextran. Polythreonine is especially preferred. The nucleic acid member is preferably an oligonucleotide. The label member is preferably a fluorescent marker, such as are available commercially, such as through Molecular Probes (Eugene, Oreg.).

Figure 3:
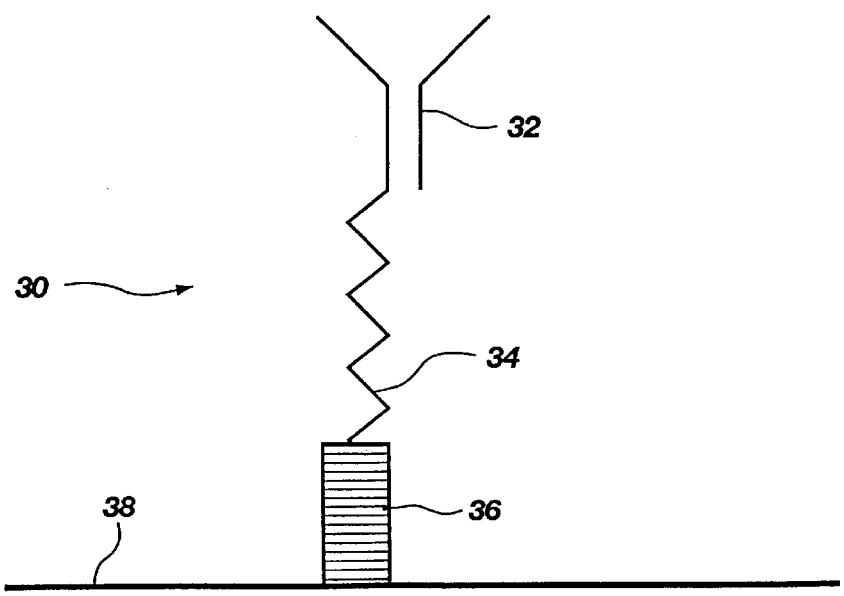
FIG. 3 shows a schematic representation of still another illustrative ligand-nucleic acid composition according to the present invention.

FIG. 3 shows a schematic representation of another illustrative composition according to the present invention. The composition 30 comprises a ligand member 32 covalently bonded to a nucleic acid member 34, which is in turn covalently bonded to a linker 36. The linker 36 is covalently bonded to a solid support 38. The ligand member, nucleic acid member, and linker can be the same. as described above for the composition described in FIG. 1. The solid support is preferably a polymer in the form of a membrane, bead, or the like. Representative suitable polymers for forming the solid support include fluorinated polymers including poly (tetrafluoroethylene) ("TEFLON"), polyvinylidene fluoride (PVDF), and the like; polyolefins such as polyethylene, ultra-high molecular weight polyethylene (UPE), polypropylene, polymethylpentene, and the like; polystyrene or substituted polystyrenes; polysulfones such as polysulfone, polyethersulfone, and the like; polyesters including polyethylene terephthalate, polybutylene terephthalate, and the like; polyacrylates and polycarbonates; and vinyl polymers such as polyvinyl chloride and polyacrylonitriles. Copolymers can also be used for forming the polymer support, such as copolymers of butadiene and styrene, fluorinated ethylene-propylene copolymer, ethylenechlorotrifluoroethylene copolymer, and the like.

Inorganic solid supports can also be used, such as ceramic materials.

The solid support can contain moieties on the surface thereof such as carboxylic acid, hydroxyl, sulfonic acid, epoxy, primary amine, and derivatized benzyl groups, as described in U.S. Pat. No. 5,547,760 (hereby incorporated by reference). The solid support is bonded to the linker component by the formation of a covalent bond. For example, the activation of a carboxylic acid group with thionyl chloride to form an acid chloride takes place according to the formula:

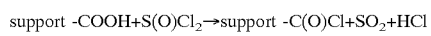
support -COOH+S(O)Cl$_2$→support -C(O)Cl+SO$_2$+HCl

Carboxylic acid groups can also be converted to acid chloride groups by the reaction with phosphorus pentachloride or phosphorus trichloride.

Linkers containing reactive amines, alcohols, thiols, Grignard reagents, and the like can be covalently bonded to the support through the C(O)Cl group as follows (where "L" signifies the linker":

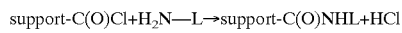
support-C(O)Cl+H$_2$N—L→support-C(O)NHL+HCl

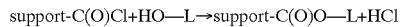
support-C(O)Cl+HO—L→support-C(O)O—L+HCl

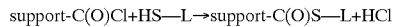
support-C(O)Cl+HS—L→support-C(O)S—L+HCl

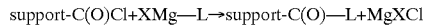
support-C(O)Cl+XMg—L→support-C(O)—L+MgXCl

In a similar manner, the activation of sulfonic acid groups is exemplified by the reaction of sulfonic acid groups with thionyl chloride to form sulfonyl chloride groups according to the formula:

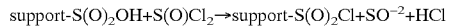
support-S(O)$_2$OH+S(O)Cl$_2$→support-S(O)$_2$Cl+SO$^{-2}$+HCl

Sulfonyl chloride groups also can be obtained by reaction of sulfonic acid groups with phosphorus pentachloride or phosphorus trichloride.

Linkers containing reactive amines, alcohols, and the like can be covalently bonded to the support through the —S(O)$_2$Cl groups as follows (where "L" signifies the linker):

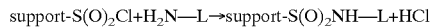
support-S(O)$_2$Cl+H$_2$N—L→support-S(O)$_2$NH—L+HCl

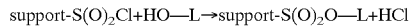
support-S(O)$_2$Cl+HO—L→support-S(O)$_2$O—L+HCl

Activation of support surfaces containing hydroxyl groups can be carried out by tosylation according to the procedure described in U.S. Pat. No. 5,416,198 (hereby incorporated by reference).

Figure 4:
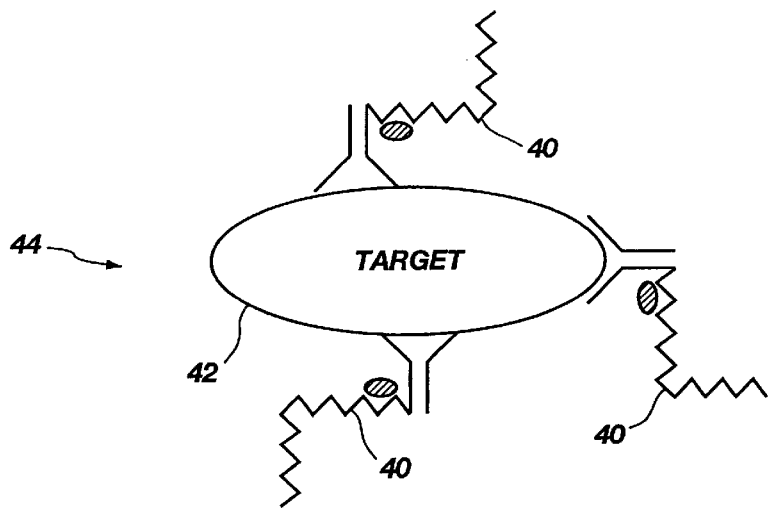
FIG. 4 shows a schematic diagram of a target bound with ligand-nucleic acid compositions.

The method of the present invention is carried out with the composition of FIG. 1 or FIG. 2 being used together with the composition of FIG. 3. The nucleic acid members of these two compositions are designed to be complementary, at least in part, as will be described in more detail below. The "free composition" of FIG. 1 or FIG. 2 is added to and mixed with an aqueous sample that is to be assayed. If the target molecule for the ligand is present in the sample, then the ligand will bind to the target. Targets can include bacteria, viruses, parasites, and other biological contaminants, as well as abiotic contaminants such as toxins, antibiotics, pesticides, and the like. FIG. 4 illustrates the binding of such compositions 40 to a target molecule 42 in the aqueous sample, thus forming a complex 44. Thus, the complex 44 comprises the target 42 labeled with the capture composition 40. The complex is then ready to be bound to a solid phase. It should be noted at this point that the aqueous sample contains capture compositions 40 that have not bound to a target. These unbound capture compositions 40 can also be bound to the solid support in the next step of the process.

Figure 5:
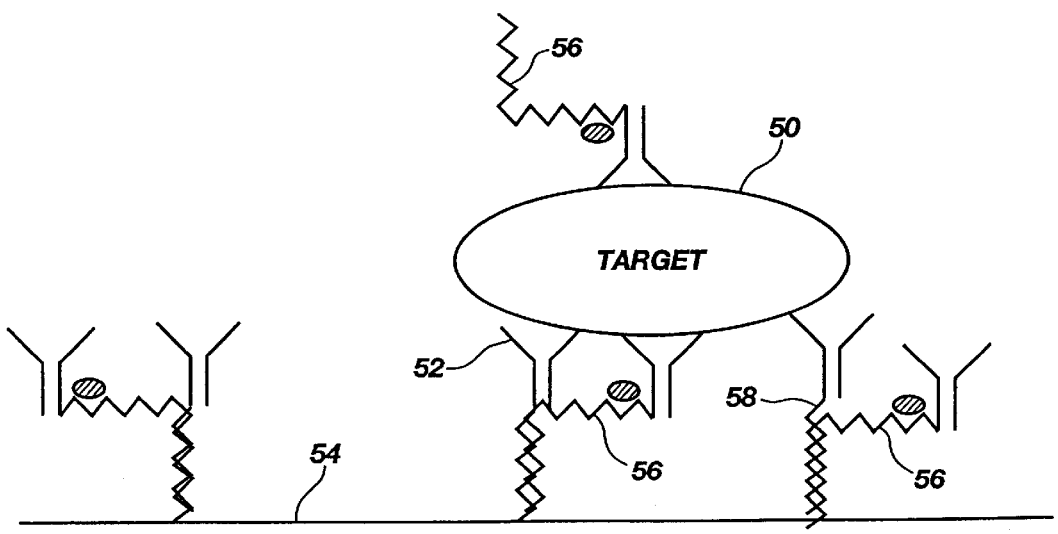
FIG. 5 shows a schematic diagram of a target bound to a solid support according to the method of the present invention.

Next, the complex is placed in contact with the solid support composition described in FIG. 3. The complex interacts with the solid support composition in two ways to result in binding of the target to the solid support. As shown in FIG. 5, the target is bound by the ligand 52 that is bound to the support 54. Further, the nucleic acid portion 56 of the free composition hybridizes with the nucleic acid portion 58 that is covalently bound to the solid support 54. Thus, the target is then bound to the surface of the solid support by DNA hybridization and by antigen-antibody affinity binding.

At this stage of the process, the ligand-nucleic acid compositions that have not formed a complex with a target entity should be removed, since they can cause a high level of background noise at the detection stage of the process. This is done by increasing the temperature to melt the DNA duplex while at the same time applying a low flow rate of aqueous medium to carry away the compositions that are released from the surface. The target complex is not released from the surface because it is bound by the antibody-antigen binding even though the DNA duplex unravels. After washing away the non-target bound ligand-nucleic acid complexes, the DNA duplex reforms. The surface of the solid support then contains only target-containing complexes. Detection of the target can be carried out with little or no background. Bacterial spores, toxins, and proteins have been detected by this methodology, and any target that can be bound by a ligand can be captured and detected in this way. For cellular targets, the viability of the cell can be estimated with the application of a vital stain or similar method of determining viability, such as with a fluorescent stain (BACLIGHT kit, Molecular Probes, Eugene, Oreg.). This stains cellular targets with fluorescent dyes, which yields an additional level of discrimination important for risk assessment.

Specificity depends on the quality and selection of the ligand (e.g. antibody) and nucleic acid (e.g. oligonucleotide) attached to the ligand. Each of these factors can be readily changed or mixed in a variety of formats to achieve the desired specificity. This challenge has been met with careful ligand screening based on the ability of the ligand to bind the target at high temperatures and salt concentrations. Additionally, the thermal melting temperature ($T_m$) of the nucleic acid duplex can be selected to be above 60° C., but below 85° C. This range allows sufficient flexibility to melt the DNA complex without denaturing the antibody and thus releasing the target. Each ligand, corresponding to a different target can have a unique oligonucleotide associated therewith. Therefore, many antibody/target complexes can be present in the sample solution, but only the complex with the oligonucleotide complementary to the support-bound oligonucleotide will be captured at the surface of the support. This has been demonstrated with antibodies against spores of *Bacillus stearothermophilus* and *Bacillus subtilis* var. *niger*. Both of these antibodies were specific for their target, and no false positives were detected.

Sensitivity depends on the ligand binding constants, the melting temperature of the oligonucleotide sequence attached to the ligand, and the fluorophore attached to the ligand via the oligonucleotide. Each of these factors can be readily changed or mixed in a variety of formats to achieve the desired specificity and sensitivity. Alternatively, a third ligand (e.g. antibody) can be used, which is labeled with an enzyme that catalyzes a hydrolysis reaction to form a fluorescent signal that can be amplified, such as described by Blake & Weimer, supra (hereby incorporated by reference). Based on the parameters described above, a sensitivity of detection of 0.1 spores/ml in 15 minutes has been achieved.

EXAMPLE 1

Bacteria. Commercial preparations of spores of *B. stearothermophilus* ATCC 10149, *B. cereus* ATCC 11778, and *B. subtilis* 6633 (Fisher Scientific, Pittsburgh, Pa.) were used as immunogens to elicit production of antibodies. Viable spore numbers and germination estimates were obtained by plating on plate count agar (PCA) overnight at 65° C. or 30° C. Spores of *B. circulans* ATCC 4513, *B. coagulans* ATCC 7050, *B. licheniformis* (raw milk isolate provided by Floyd Bodyfelt, Oregon State University), *B. mascerans* (raw milk isolate provided by Floyd Bodyfelt, Oregon State University), *B. polymyxa* ATCC 842, and *B. pumulus* (raw milk isolate provided by Floyd Bodyfelt, Oregon State University), were prepared by plate spreading a single colony isolate on PCA and incubating the covered plate at 30° C. for about 2 weeks. Spores were swabbed from the surface of the agar and washed repeatedly in distilled water to remove water-soluble components. Spores were pelleted and separated from cell debris by centrifugation (1500×g for 20 minutes at 4° C.). D. E. Gombas & R. F. Gomez, Sensitization of *Clostridium perfringens* Spores to Heat by Gamma Radiation, 36 Appl. Environ. Microbiol. 403–407 (1987). Presence of spores was confirmed by heating to 80° C. for 15 minutes and then plating on PCA. G. H. Richardson, supra; P. Patel, Rapid Analysis Techniques in Food Microbiology (1994). Presence of an exosporium on the spore was tested by phase contrast microscopy with crystal violet staining. C. Du & K. Nickerson, *Bacillus thuringiensis* HD-73 Spores Have Surface-localized Cry Ac Toxin: Physiological and Pathogenic Consequences, 62 Appl. Environ. Microbiol. 3722–3726 (1996).

EXAMPLE 2

Polyclonal antibody production. Polyclonal antibodies against *B. stearothermophilus*, *B. subtilis*, and *B. cereus* spores were made by injecting BALB/c mice in the intraperitoneal cavity with 1×10$^7$ cfu/ml of cells or spores in sterile saline (0.5 ml) three times at 3-week intervals. E. Harlow & D. Lane, Antibodies, A Laboratory Manual (1988). IgG was purified using a protein A/G column (Pierce Chemical, Rockford, Ill.). Antibodies were desalted and concentrated to 1 mg/ml in 0.1 M sodium phosphate, pH 7.0, in a 30 kcDa Centricon (Amicon, Beverly, Mass.) at 4500×g at 4° C.

EXAMPLE 3

Monoclonal antibodies. Monoclonal, antibodies were produced against *B. stearothermophilus* by suspending cells or spores in PBS to an absorbance of 0.93 at 550 nm before injecting female BALB/c mice intraperitoneally with 0.250 m g (whole cell wet weight) without adjuvant. The mice were immunized three times at 3-week intervals. Seven days after the last immunization they were test bled, and the serum was titered by ELISA three days before fusion. Booster injections were administered by intraperitoneal injection with 0.1 mg of cells in PBS. Fusion with a compatible murine myeloma cell line (P3X63-Ag8.653) was done in the presence of polyethylene glycol. Selection for hybrid cells was done in HAT medium. E. Harlow & D. Lane, supra; G. Kohler & C. Milstein, Continuos Cultures of Fused Cells Secreting Antibody of Pre-defined Specificity, 256 Nature 495–597 (1975); hereby incorporated by reference. Positive colonies were determined by ELISA and subcloned twice before freezing in liquid nitrogen.

EXAMPLE 4

Antibodies prepared according to the procedure of Example 2 or 3 were prepared for conjugation by oxidation with sodium meta-periodate as described in G. T. Hermanson et al., Immobilized Affinity Ligand Techniques (1992), hereby incorporated by reference. After oxidation, the sodium meta-periodate was removed by washing five times with 0.1 M sodium phosphate, pH 7.0, in a 30 kDa Centricon (4500×g, 4° C.) and immediately subjected to crosslinking.

PolyThr (MW(vis) 12,100; Sigma Chemical Co., St. Louis, Mo.) was covalently coupled to a 2.8 $\mu$m, tosyl-activated polystyrene bead (Dynal, Lake Success, N.Y.) in 50 mM borate buffer (pH 9.5) via the terminal amine, as descrbed in the product literature. Four washes (three times for 10 minutes each, and once for 30 minutes) with TBS buffer (pH 7.5) were used to block remaining tosyl-active sites. Adenine dihydrazine (ADH; 0.5 M in 0.1 M MES, pH 4,75; Sigma) was linked to the carboxy terminus of the bound PolyThr using an ethylene diamine carbodiimide mediated reaction. G. T. Hermanson et al., supra. After crosslinking, the immunomagnetic beads were stored rotating (50 rpm) in PBST with 0.02% sodium azide at 4° C. until use.

Oligonucleotides can be conjugated to the PolyThr linker according to methods well known in the art, e.g. T. Zhu et al., 3 Antisense Res. Dev. 265 (1993); T. Zhu et al., 89 Proc. Nat'l Acad. Sci. USA 7934 (1992); P. Rigaudy et al., 49 Cancer Res. 1836 (1989), which are hereby incorporated by reference.

EXAMPLE 5

Ceramic (metal oxide) beads, 7 mm in diameter (Coors Ceramics Corp., Golden, Colo.) were washed in acidic methanol (HCl:methanol, 1:1) for 30 minutes at room temperature to strip the bead surface. The acidic methanol was poured off and the beads rinsed several times with filtered water (dH$_2$O). The beads were further washed with concentrated sulfuric acid three times for 30 minutes, rinsed several times with dH$_2$O, and finally boiled in dH$_2$O for 30 minutes to introduce hydroxyl groups onto the surface.

For silanizing and crosslinking, beads were air dried, washed once in toluene, and incubated in 3% 3-mercaptopropyltrimethoxysilane(3% MTS in toluene) for 2 hours at room temperature. Later, the beads were prepared for the addition of the crosslinker γ-maleimidobutryic acid N-hydroxy succinimide ester (GMBS; Sigma). Beads were washed twice in toluene to remove the unbound MTS, air dried, introduced to 2 mM GMBS (in 100% ethanol), and incubated for 1 hour at room temperature. Beads were finally washed in 100% ethanol and subsequently washed with PBS.

Dextran was coupled to the beads as follows. Sodium-m-periodate (Sigma) was used to oxidize the carbohydrate moieties on the dextran (37.5 kDa, Sigma) for 3 hours at room temperature while shaking. The salt was removed by washing four times with dH$_2$O in a 30 kDa Centricon and immediately bound to the crosslinked beads. Adipic acid dihydride (ADH, 0.5 M in sodium phosphate, pH 7.2; Sigma) was then added to introduce an amine group to the bead surface that could then react with an oligonucleotide-antibody. All unreacted sites were blocked with 1% tris/bsa, ph 8.5.

I claim:

1. A method for capturing a target on a solid support comprising:
   (a) mixing an aqueous sample containing the target with a first composition comprising a first ligand component, configured for binding the target, covalently bonded to a first nucleic acid component such that the first ligand component binds the target to result in a complex;
   (b) contacting the mixed sample with a second composition comprising (i) a solid support covalently bonded to a linker, (ii) a second nucleic acid component covalently bonded to the linker wherein the second nucleic acid component is complementary to at least a portion of the first nucleic acid component and hybridizes thereto when in contact therewith, resulting in a duplex that has a thermal melting temperature of about 60–85° C., and (iii) a second ligand component covalently bonded to the second nucleic acid component, such that the second nucleic acid component hybridizes to the first nucleic acid component and the second ligand component binds the target;
   (c) heating the contacted sample to a temperature above the thermal melting temperature of the duplex without denaturing the first ligand component or second ligand component and causing the heated aqueous sample to flow by the solid support, thereby washing away non-target bound first ligand-first nucleic acid component conjugates; and
   (d) then reducing the temperature of the heated sample to ambient temperature, thereby capturing the target on the solid support.

2. The method of claim 1 wherein said first and second ligand components are independently selected from the group consisting of antibodies, antigens, lectins, saccharides, and gangliosides.

3. The method of claim 1 wherein said linker is polythreonine.

4. The method of claim 1 wherein said linker is polyserine.

5. The method of claim 1 wherein said linker is dextran.

6. The method of claim 1 wherein the first and second nucleic acid components are oligonucleotides.

7. The method of claim 6 wherein the first and second ligand components are antibodies.

8. The method of claim 7 wherein the linker is polythreonine.

9. The method of claim 8 wherein the solid support comprises a membrane and said membrane is a member selected from the group consisting of fluorinated polymers, polyolefins, polystyrene, substituted polystyrenes, polysulfones, polyesters, polyacrylates, polycarbonates, vinyl polymers, copolymers of butadiene and styrene, fluorinated ethylene-propylene copolymers, ethylenechorotrifluoroethylene copolymers, and mixtures thereof.

10. The method of claim 8 wherein the solid support comprises a bead and said bead is a member selected from the group consisting of silicon, glass, silica, quartz, metal oxides, polyvinyl alcohol, polystyrene, poly(acrylic acid), and mixtures thereof.

11. The method of claim 6 wherein the second ligand component is an antibody.

12. A method for determining an amount of a target in an aqueous sample containing or suspected of containing the target, comprising:
(a) mixing the aqueous sample with a first composition comprising (i) a first ligand component, configured for binding the target, (ii) a first nucleic acid component covalently bonded to said first ligand component, and (iii) a label component covalently bonded to said first nucleic acid component, such that the first ligand component binds the target to result in a complex;
(b) contacting the mixed sample with a second composition comprising (i) a solid support covalently bonded to a linker, (ii) a second nucleic acid component covalently bonded to the linker wherein the second nucleic acid component is complementary to at least a portion of the first nucleic acid component and hybridizes thereto when in contact therewith, resulting in a duplex that has a thermal melting temperature of about 60–85° C., and (iii) a second ligand component covalently bonded to the second nucleic acid component, such that the second nucleic acid component hybridizes to the first nucleic acid component and the second ligand component binds the target;
(c) heating the contacted sample to a temperature above the thermal melting temperature of the duplex without denaturing the first ligand component or the second ligand component and causing the heated aqueous sample to flow by the solid support, thereby washing away non-target bound first ligand-first nucleic acid component conjugates;
(d) then reducing the temperature of the heated sample to ambient temperature; and
(e) determining an amount of the label component on the solid support, wherein the amount of label indicates the amount of the target in the aqueous sample.

13. The method of claim 12 wherein the first and second nucleic acid components are oligonucleotides.

14. The method of claim 12 wherein the first and second ligand components are independently selected from the group consisting of antibodies, antigens, lectins, saccharides, and gangliosides.

15. The method of claim 12 wherein said first and second ligand components are antibodies.

16. The method of claim 12 wherein said linker is polythreonine.

17. The method of claim 12 wherein said linker is polyserine.

18. The method of claim 12 wherein said linker is dextran.

19. The method of claim 12 wherein the solid support comprises a membrane and said membrane is a member selected from the group consisting of fluorinated polymers, polyolefins, polystyrene, substituted polystyrenes, polysulfones, polyesters, polyacrylates, polycarbonates, vinyl polymers, copolymers of butadiene and styrene, fluorinated ethylene-propylene copolymers, ethylenechlorotrifluoroethylene copolymers, and mixtures thereof.

20. The method of claim 12 wherein the solid support comprises a bead and said bead is a member selected from the group consisting of silicon, glass, silica, quartz, metal oxides, polyvinyl alcohol, polystyrene, poly(acrylic acid), and mixtures thereof.

* * * * *